(12) United States Patent
Pion

(10) Patent No.: US 9,304,098 B2
(45) Date of Patent: Apr. 5, 2016

(54) CAPACITIVE HUMIDITY SENSOR WITH HYSTERESIS COMPENSATION

(71) Applicant: Veris Industries, LLC, Tualatin, OR (US)

(72) Inventor: Albert Pion, Tigard, OR (US)

(73) Assignee: Veris Industries, LLC, Tualatin, OR (US)

( * ) Notice: Subject to any disclaimer, the term of this patent is extended or adjusted under 35 U.S.C. 154(b) by 241 days.

(21) Appl. No.: 14/092,410

(22) Filed: Nov. 27, 2013

(65) Prior Publication Data

US 2014/0218055 A1  Aug. 7, 2014

Related U.S. Application Data

(60) Provisional application No. 61/760,613, filed on Feb. 4, 2013.

(51) Int. Cl.
*G01N 27/22* (2006.01)
(52) U.S. Cl.
CPC ............ *G01N 27/225* (2013.01); *G01N 27/228* (2013.01)
(58) Field of Classification Search
CPC .................................................... G01N 27/225
USPC ................................. 324/665, 669
See application file for complete search history.

(56) References Cited

U.S. PATENT DOCUMENTS

| | | | |
|---|---|---|---|
| 4,806,847 A * | 2/1989 | Atherton | G01F 23/268 324/665 |
| 5,161,085 A | 11/1992 | Sakai et al. | |
| 5,177,662 A | 1/1993 | Thoma | |
| 5,296,819 A | 3/1994 | Kuroiwa et al. | |
| 5,345,821 A | 9/1994 | Reich et al. | |
| 5,348,761 A | 9/1994 | Mitter et al. | |
| 5,408,381 A | 4/1995 | Thoma et al. | |
| 5,434,737 A | 7/1995 | Miura | |
| 5,644,080 A | 7/1997 | Stormbom et al. | |
| 6,342,295 B1 | 1/2002 | Kobayashi | |
| 6,580,600 B2 | 6/2003 | Toyoda et al. | |
| 6,647,782 B2 | 11/2003 | Toyoda | |
| 6,724,612 B2 | 4/2004 | Davis et al. | |
| 7,012,798 B2 | 3/2006 | Naito et al. | |
| 7,032,448 B2 * | 4/2006 | Hamamoto | G01N 27/225 361/280 |
| 7,049,829 B2 * | 5/2006 | Luthi | G01N 27/225 324/664 |
| 7,430,904 B2 | 10/2008 | Isogai et al. | |
| 2008/0257037 A1 * | 10/2008 | Isogai | G01N 27/225 73/335.04 |
| 2012/0247203 A1 | 10/2012 | Zhang et al. | |
| 2014/0216153 A1 * | 8/2014 | Pion | G01N 27/225 73/335.04 |

* cited by examiner

*Primary Examiner* — Tung X Nguyen
*Assistant Examiner* — Robert P Alejnikov, Jr.
(74) *Attorney, Agent, or Firm* — Chernoff Vilhauer McClung & Stenzel, LLP

(57) ABSTRACT

A gas sensing device that includes differential temperature compensation.

7 Claims, 7 Drawing Sheets

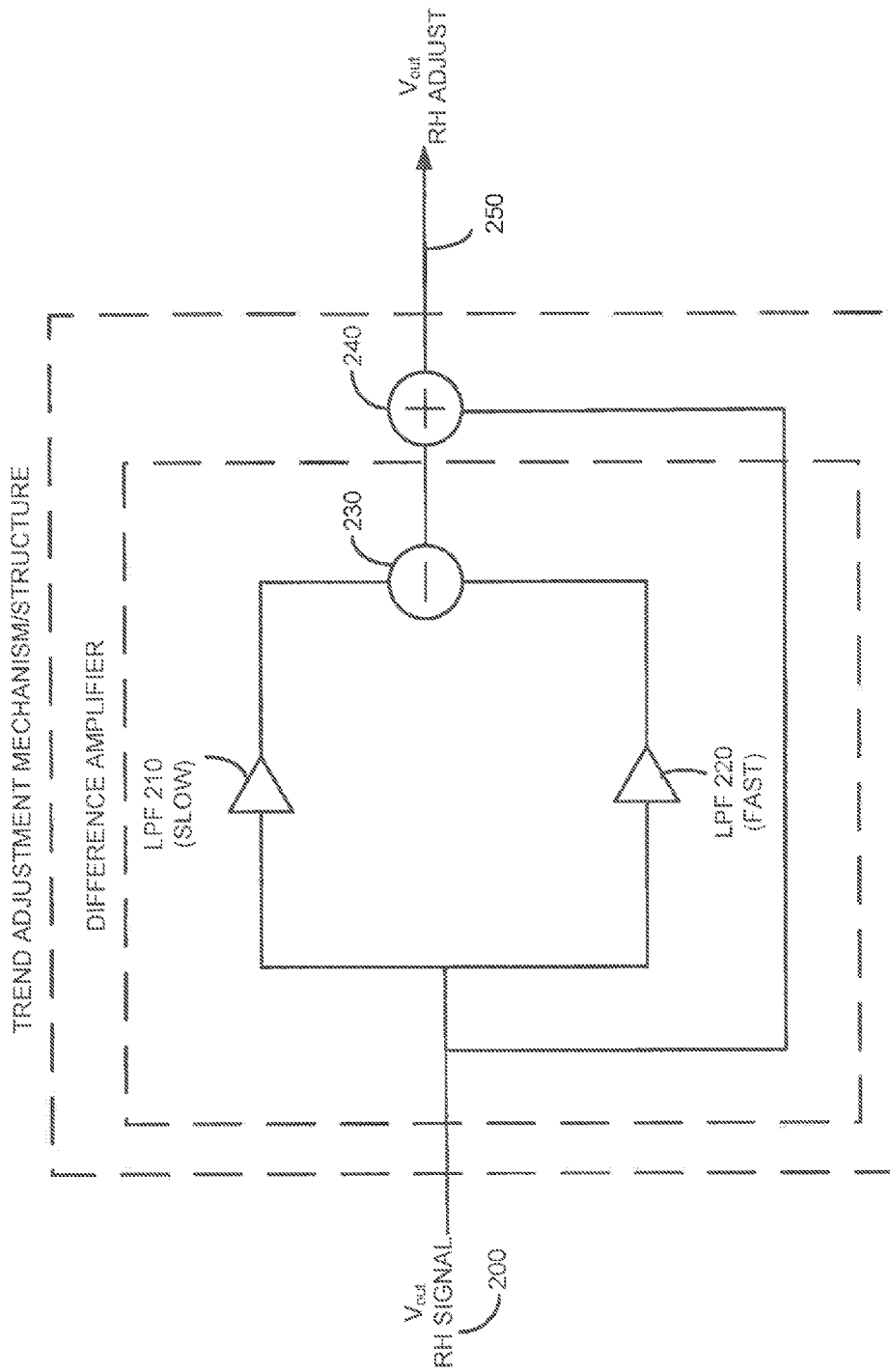

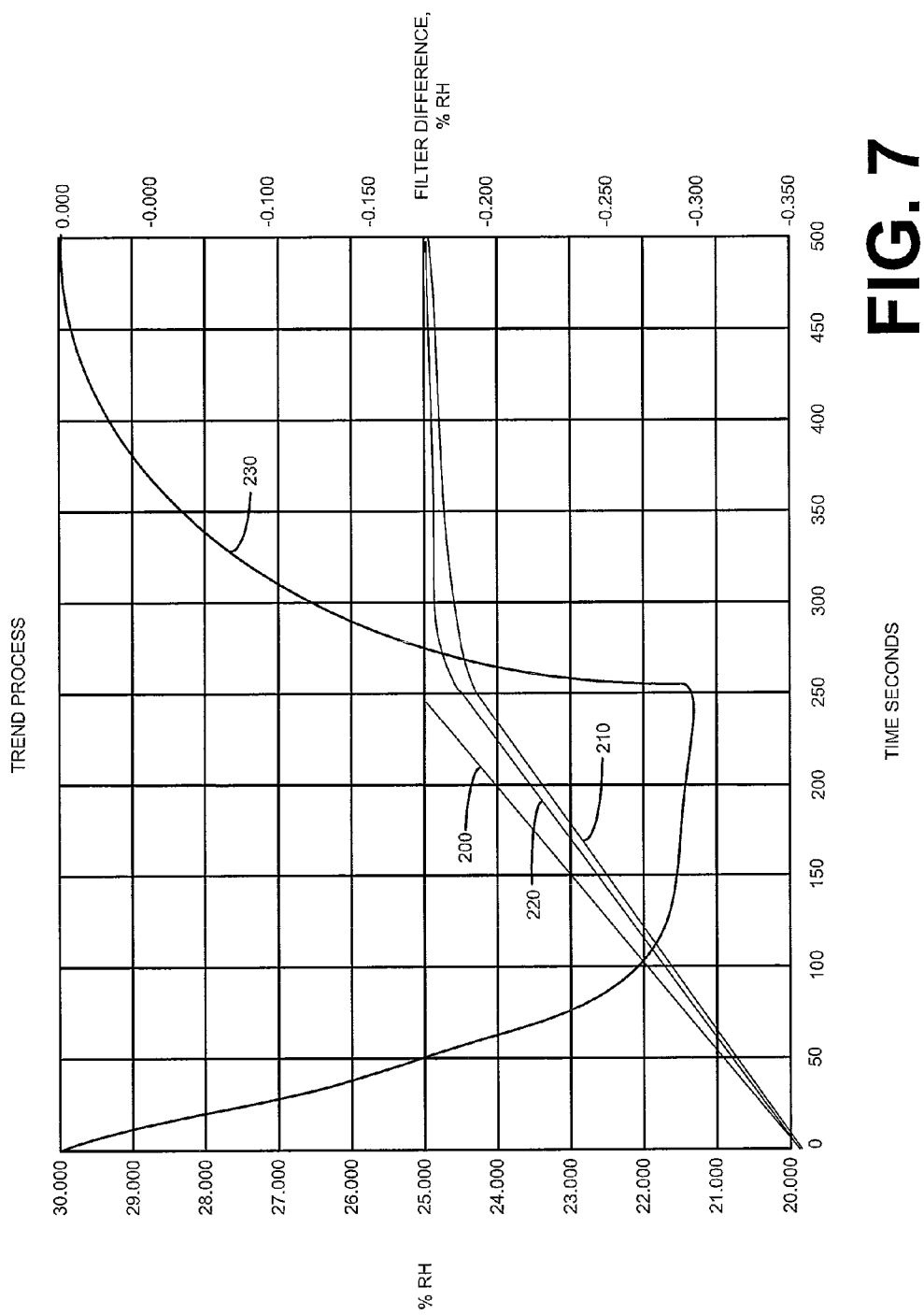

CAPACITIVE HUMIDITY SENSOR WITH HYSTERESIS COMPENSATION

CROSS-REFERENCE TO RELATED APPLICATIONS

This application claims the benefit of U.S. Provisional App. No. 61/760,613, filed Feb. 4, 2013.

BACKGROUND OF THE INVENTION

The present invention relates generally to a capacitive humidity sensor with hysteresis compensation.

A humidity sensor is a device used for measuring the moisture content in an environment. Humidity sensors typically rely on the measurement of some other property than humidity such as a change in mass, a change in electrical capacitance, and/or a change in electrical resistance of a substance as moisture is absorbed or discharged. In particular, with respect to capacitive based humidity sensors, the humidity has an effect on a dielectric constant of a polymer substance, metal oxide substance, or otherwise. The change in the dielectric constant is measured to determine the humidity. Unfortunately, the accuracy of humidity sensors is limited due to many factors, including for example, temperature, contamination, drift, hysteresis, and/or aging effects.

What is desired therefore is a capacitive humidity sensor with compensation to improve its accuracy.

The foregoing and other objectives, features, and advantages of the invention may be more readily understood upon consideration of the following detailed description of the invention, taken in conjunction with the accompanying drawings.

BRIEF DESCRIPTION OF THE SEVERAL VIEWS OF THE DRAWINGS

FIG. 6 illustrates a trend process.
FIG. 7 illustrates curves for the trend process.

DETAILED DESCRIPTION OF PREFERRED EMBODIMENT

Figure 1:
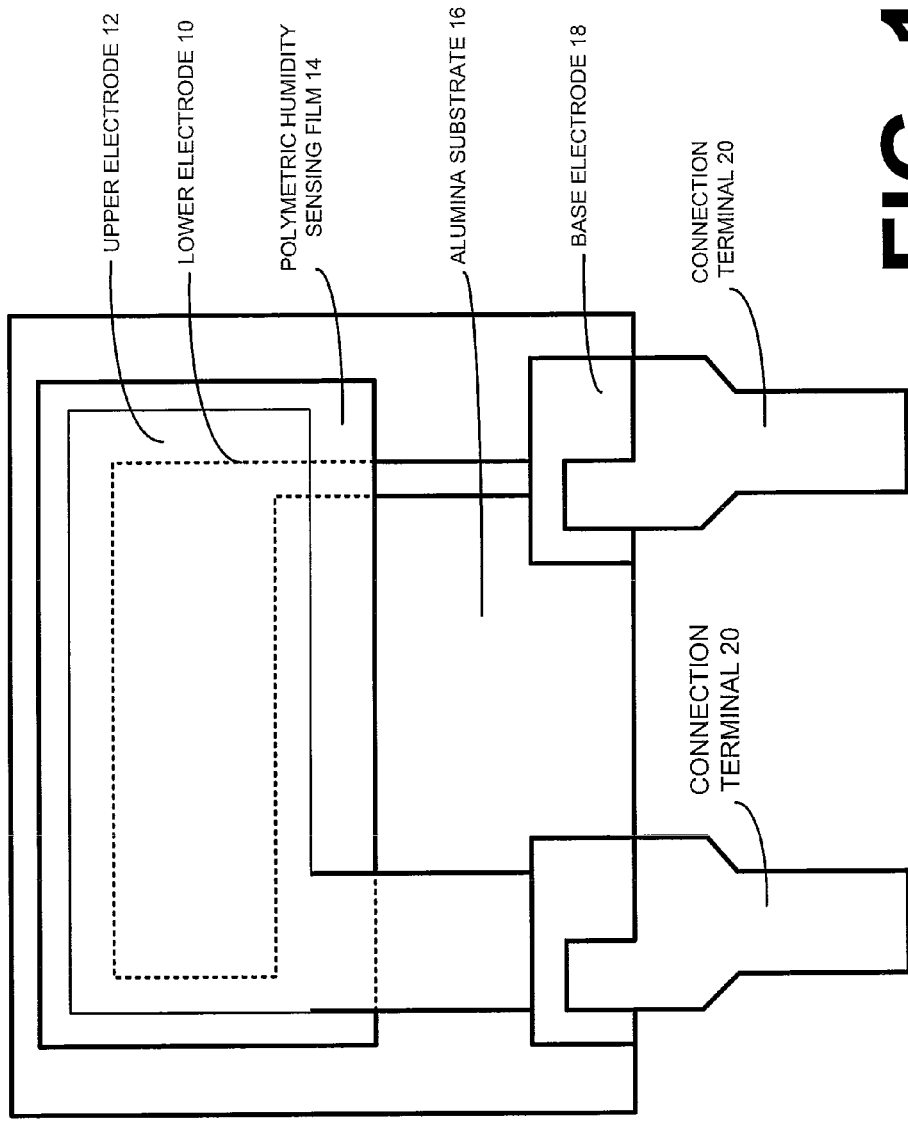
FIG. 1 illustrates a cut away of a capacitive sensor.

Referring to FIG. 1, an exemplary capacitive humidity sensor is illustrated. Humidity sensors relying on this principle may consist of a hygroscopic dielectric material sandwiched between a pair of electrodes, namely a lower electrode 10 and an upper electrode 12, forming a small capacitor. Most capacitive sensors use a plastic or polymer as the dielectric material 14, with a typical dielectric constant ranging from 2 to 15. The capacitive sensor may include an alumina substrate 16, a base electrode 18, and connection terminals 20. In absence of moisture, the dielectric constant of the hygroscopic dielectric material 14 and the sensor geometry determine the value of capacitance. At typical room temperature, the dielectric constant of water vapor may have a value of about 80, a value which is substantially larger than the constant of the sensor dielectric material. Therefore, subsequent absorption of water vapor by the sensor results in an increase in sensor capacitance. At equilibrium conditions, the amount of moisture present in a hygroscopic material 14 primarily depends on both the ambient temperature and the ambient water vapor pressure. At equilibrium conditions, of the amount of moisture present in a hygroscopic material primarily depends on both the ambient temperature and the ambient water vapor pressure are likewise applicable to any hygroscopic dielectric material used on the sensor.

Relative humidity is a function of both the ambient temperature and water vapor pressure. Therefore there is a relationship between relative humidity, the amount of moisture present in the sensor, and sensor capacitance. This relationship primarily governs the operation of the capacitive humidity sensor.

On an alumina substrate 16, the lower electrode 10 is often formed using gold, platinum and/or other material. The polymer layer 14 such as polyvinyl alcohol (PVA) is deposited on the lower electrode 10. This polymer layer 14 senses the ambient humidity. On top of this polymer layer 14, a gold upper layer 12 (or other material) is deposited which acts as a top electrode. The upper electrode 12 also allows water vapor to pass through it, into the sensing polymer layer 14. The water vapors enter and/or leave the hygroscopic sensing layer until the vapor content is in equilibrium with the ambient air or gas. Accordingly, preferably the capacitive humidity sensor is principally a capacitive element that includes a humidity sensitive material therein. As the relative humidity increases the capacitance increases. As the relative humidity decreases the capacitance decreases. The relative percentage of the actual vapor pressure (P) compared to the saturated vapor pressure ($P_s$) may be characterized as follows: RH = $(P/P_s)*100\%$. Other types of capacitive humidity sensors may likewise be used, such as for example, multi-walled carbon nanotubes.

Figure 2:
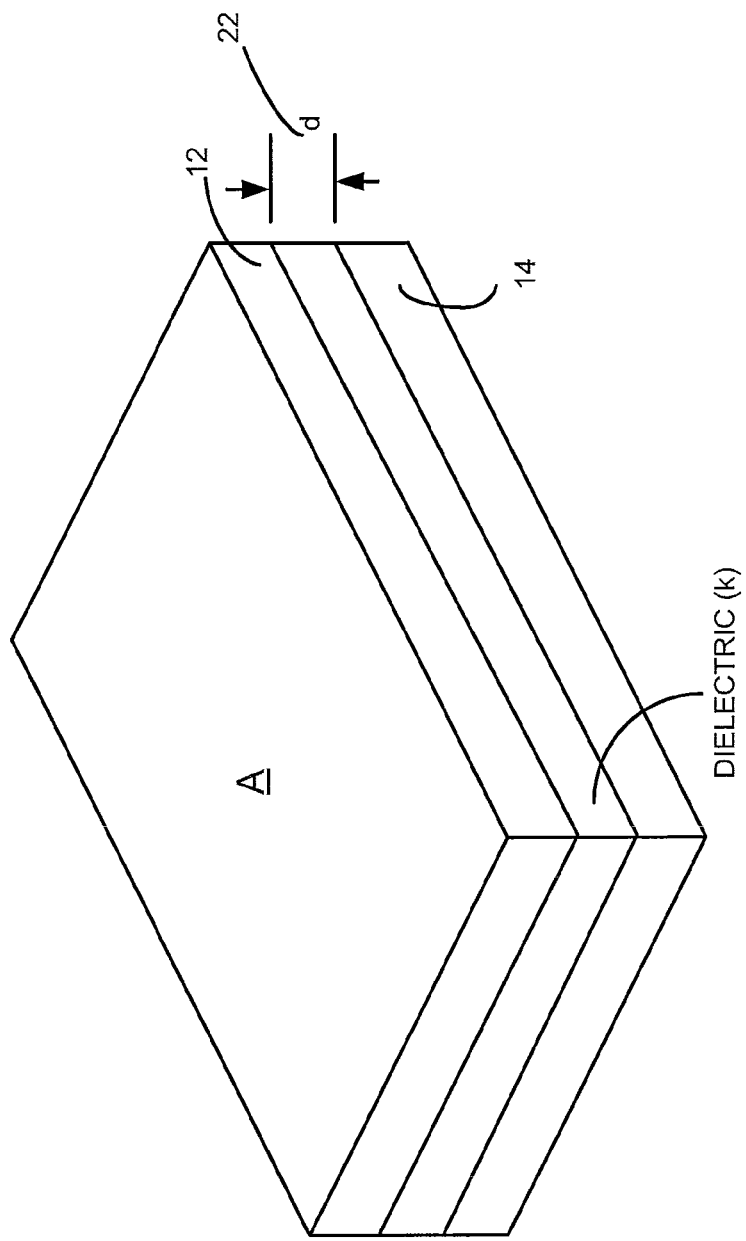
FIG. 2 illustrates layers of a capacitive sensor.
Figure 3:
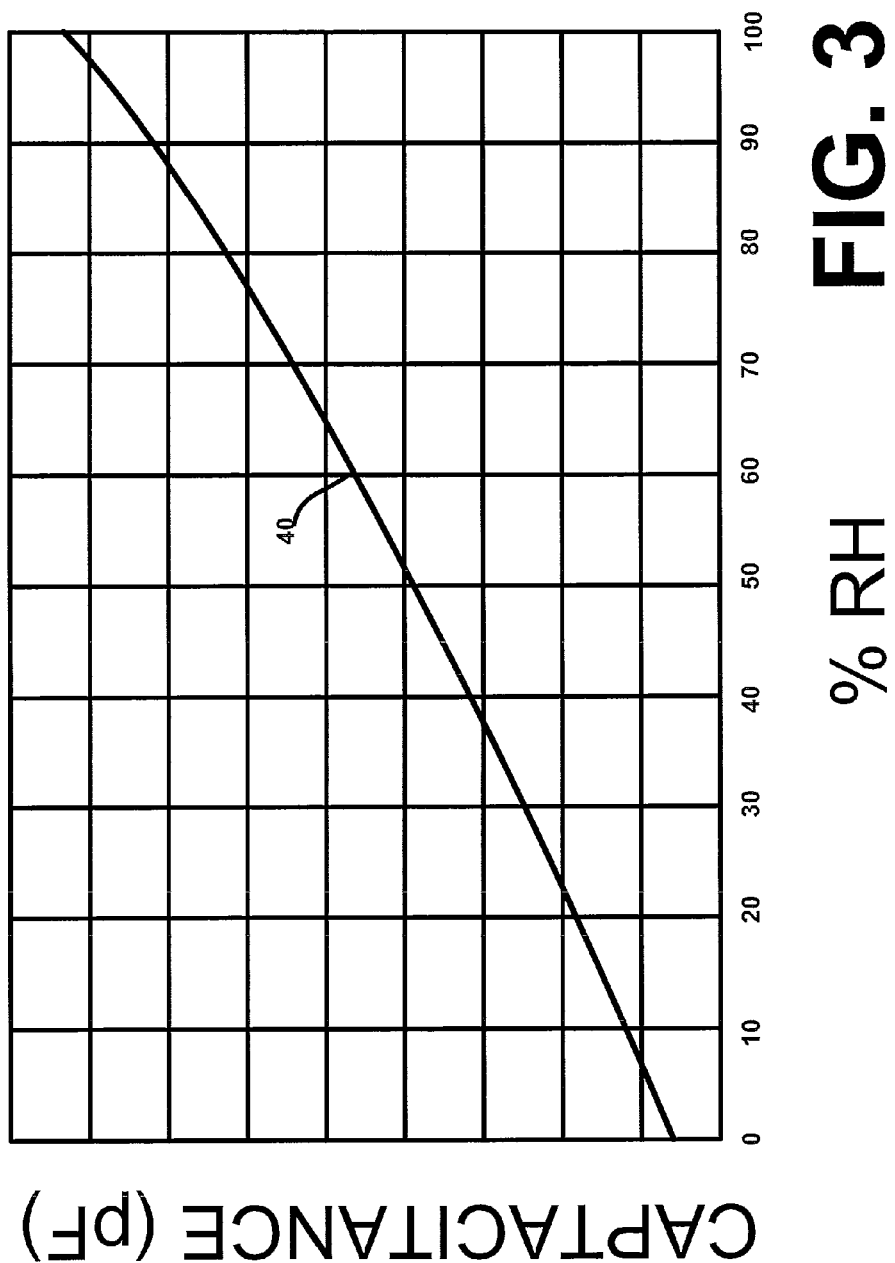
FIG. 3 illustrates a capacitance versus relative humidity graph.

Referring to FIG. 2, the capacitance is dependent on the constant (k) of the dielectric, which is in turn dependent on the relative humidity and temperature (T) of the dielectric. This relationship may be characterized as $C=k_0 * \epsilon_o * A/d$, where d is the distance 22 between the conductive layers 12, 14, and A is the area of the conductive plates. For moist air the dielectric may be calculated by the following relationship, $k=1+(211/T)*(P+(48P_s/T)*RH)*10^{-6}$, where k typically has a linear relationship to the relative humidity (RH) and the capacitance has a non-linear relationship to the relative humidity. Referring to FIG. 3, this non-linear relationship 40 is characterized for the sensor so that the device may be calibrated.

Figure 4:
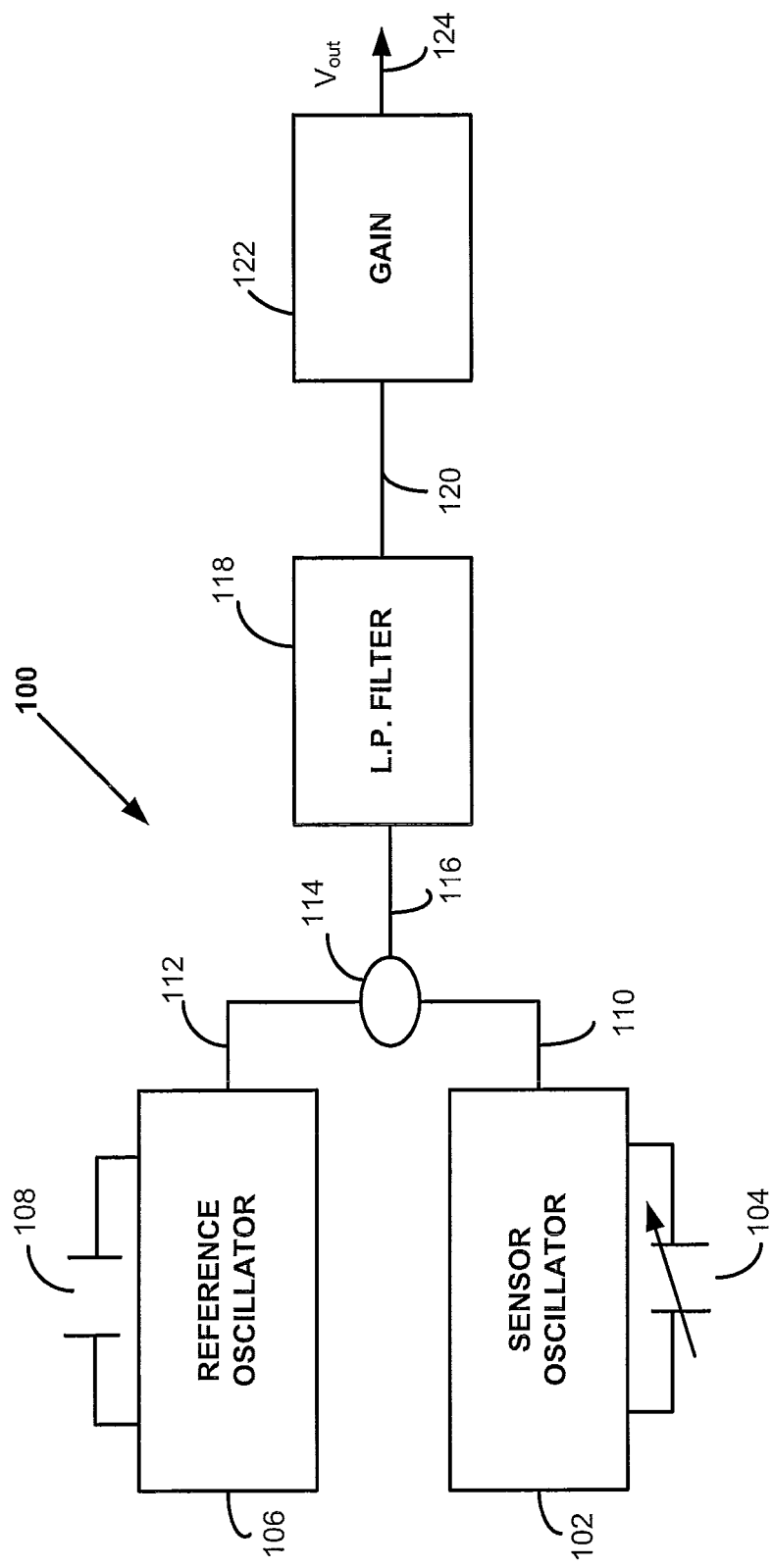
FIG. 4 illustrates a capacitance detector circuit.

Referring to FIG. 4, one exemplary technique to sense the changing capacitance of the sensor is to use a signal conditioning circuit 100. A sensor oscillator 102 changes it oscillation frequency based upon a change in the capacitance 104 of a sensor. A reference oscillator 106 has a fixed oscillation frequency that is based upon the reference capacitor 108. The output 110 of the sensor oscillator 102 and the output 112 of the reference oscillator are combined 114 with a combiner with one another to provide a signal 116 that is related to a change in the sensor oscillator capacitance 104. A low pass filter 118 attenuates the oscillation frequencies leaving a voltage response 120 that is related to the change in the sensor oscillator capacitance 104. An amplifier 122 amplifies the voltage response 120 to a desired output voltage range 124.

Unfortunately, the process by which the gaseous molecules enter and leave the sensor material is non-linear and complicated. For example, typically the sensor is calibrated to an operating range before being used. Often the calibration is inaccurate due to in-batch variations, batch-to-batch variations, limited precision of a calibration reference, and the lack of stability of the sensors over time. In addition to such calibration inaccuracies, a hysteresis exists in the sensor material at different points accruing from a dry environment on the one hand and a humid environment on the other hand, provided enough dwell time exists at each point. Thus, the humidity sensor carries some memory of the conditions experienced in the recent past. Sensors with dry history tend to carry some negative offset while sensors with a humid history tend to carry some positive offset. In general, the hysteresis does not depend on the quality of the calibration but is dependent on the exposure range of the sensor, and provides yet another limitation for accurate measurements.

Figure 5:
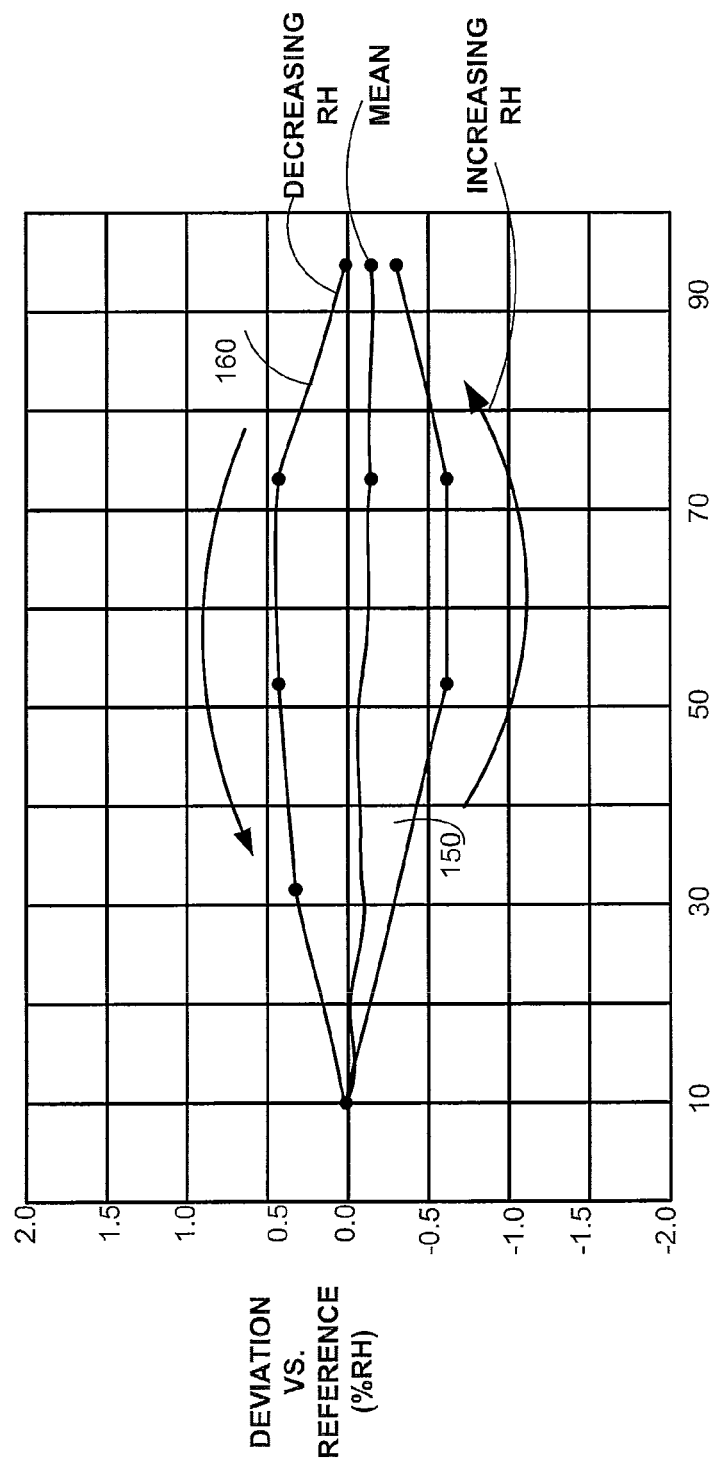
FIG. 5 illustrates hysteresis curves.

Referring to FIG. 5, while improved calibration is of assistance in obtaining improved measurements from the humidity sensor, one of the principal limitations remains the hysteresis. With the hysteresis having differences that either underestimate 150 the humidity or overestimate 160 the humidity based upon the history of the previous humidity, it was further determined that the offset in the estimation is generally proportional to the rate of change of humidity. This generally proportional rate of change of humidity may be used to estimate the amount of hysteresis error from the sensor reading.

In a rising humidity trend the sensors tends to under-estimate the actual humidity because of its hysteresis so a trend based process, such as a difference amplifier, may be used to modify the output of the sensor's humidity value toward a more accurate value. In a falling humidity trend the sensors tend to over-estimate the actual humidity because of its hysteresis so a trend based process, such as a difference amplifier, may be used to modify the output of the sensor's humidity value toward a more accurate value.

Referring to FIG. 6, the trend based process may consist of two low-pass filters 210, 220 with different time constants. One low pass filer 220 has a short (fast) time constant, while the other low pass filer 210 has a long (slow) time constant. These low pass filters operate in a manner similar to the estimation of moving averages, with the fast filter 220 being akin to a multi-day moving average and the slow filter 210 being akin to a multi-week moving average.

The output of the filters 210, 220 are subtracted 230 by a sub tractor from one another. Other trend based processes may likewise be used.

Referring also to FIG. 7, when the moving averages change direction, the lines of the moving averages cross. The difference between the lines provides an indication of how fast the change is occurring, with the trend based process determining the difference. The output of the trend detector 230 may be added 240 by an adder to the output 200 of the humidity sensor, both of which may be scaled, as appropriate. An adjusted humidity sensor output 250 is provided.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. A humidity sensor comprising:
   (a) a humidity sensitive element that estimates ambient humidity based upon a capacitive measurement to provide humidity data related to said ambient humidity;
   (b) a trend adjustment structure that modifies said humidity data based upon a rate of a temporal trend of said humidity data.

2. The humidity sensor of claim 1 wherein said humidity sensitive element includes a hygroscopic dielectric material sandwiched between a pair of electrodes.

3. The humidity sensor of claim 2 wherein said humidity sensitive element includes a signal conditioning circuit.

4. The humidity sensor of claim 1 wherein said trend adjustment structure uses a difference based comparison.

5. The humidity sensor of claim 4 wherein said difference based comparison includes a difference amplifier.

6. The humidity sensor of claim 1 wherein said adjustment mechanism modifies said humidity data based upon a generally proportional rate of change of said humidity data.

7. The humidity sensor of claim 1 wherein said adjustment mechanism modifies said humidity data using a pair of filters each of which have a different time constant.

* * * * *